US006140506A

United States Patent [19]
Baba et al.

[11] Patent Number: 6,140,506
[45] Date of Patent: Oct. 31, 2000

[54] OXAZOLIDINONE COMPOUNDS AND PROCESS FOR THE PREPARATION THEREOF

[75] Inventors: Akio Baba, Suita; Kenji Suzuki, Funabashi; Yoshinobu Yanagawa, Funabashi; Yoko Ohkuni, Funabashi; Takashi Oda, Funabashi; Masao Shimada, Funabashi; Masami Kozawa, Funabashi, all of Japan

[73] Assignee: Nissan Chemical Industries, Ltd., Tokyo, Japan

[21] Appl. No.: 09/222,918

[22] Filed: Dec. 30, 1998

Related U.S. Application Data

[63] Continuation-in-part of application No. PCT/JP97/02342, Jul. 7, 1997.

[30] Foreign Application Priority Data

Jul. 8, 1996 [JP] Japan ..................................... 8-177774

[51] Int. Cl.$^7$ ................................................. C07D 263/62
[52] U.S. Cl. ........................... 548/221; 548/215; 548/217
[58] Field of Search ...................... 548/221, 217

[56] References Cited

FOREIGN PATENT DOCUMENTS 7-316106   5/1995   Japan .

OTHER PUBLICATIONS

Herweh, J. E. et al., "2–Oxazolidones via the Lithium Bromide Catalyzed Reaction of Isocyanates with Epoxides in Hydrocarbon Solvents," *Tetrahedron Letters* No. 12, 1971, pp. 809–812.

Speranza, George P. et al., "Preparation of Substituted 2–Oxazolidones from 1,2–Epoxides and Isocyanates," *J. Org. Chem.* vol. 23, 1958, 1922–1924.

Herweh, John E. et al., "Synthesis and Nuclear Magnetic Resonance Spectra of 2–Oxazolidones," *J. Org. Chem.*, vol. 33, No. 11, 1968, pp. 4029–4033.

Tucker, Thomas J. et al., "A Series of Potent HIV–1 Protease Inhibitors Containing a Hydroxyethyl Secondary Amine Transition State Isostere: Synthesis, Enzyme Inhibition, and Antiviral Activity," *J. Med. Chem.*, vol. 35, 1992, pp. 2525–2533.

Young, Steven D. et al., "HIV–1 Protease Inhibitors Based on Hydroxyethylene Dipetide Isosteres: An Investigation into the Role of the $P_{1'}$ Side Chain on Structure–Activity," *J. Med. Chem.*, vol. 35, 1992, pp. 1702–1709.

Thompson, Wayne J. et al., "Synthesis and Antiviral Activity of a Series of HIV–1 Protease Inhibitors with Functionality Tethered to the $P_1$ or $P_{1'}$ Phenyl Substituents: X–ray Crystal Structure Assisted Design," *J. Med. Chem.*, vol. 35, 1992, pp. 1685–1701.

Lutz, Robert E. et al., "Futher Studies on the Stability of β–Hydroxyethylamines toward the Oppenauer Oxidation. cis–and trans–1–Amino–2–indanols," *J. Am. Chem. Soc.*, vol. 73, Apr. 1951, pp. 1639–1941.

Hassner, Alfred et al., "Addition of Iodine Isocyanate to Olerfins. Scope and Synthetic Utility," *J. Org. Chem.*, vol. 32, 1967, pp. 540–549.

Shibata, Ikuya et al., "Cycloaddition Reaction of Heterocumulenes with Oxirances Catalyzed by an Organotin Iodide–Lewis Base Complex," *J. Org. Chem.*, vol. 51, 1986, pp. 2177–2184.

Fujiwara, Masahiro et al., "Cycloaddition Reaction of 2,3–Disubstituted Oxiranes with Isocyanates by Highly Activated Catalyst: $Ph_4SbI-Bu_3SnI$," *Chemistry Letters*, 1986, pp. 1963–1966.

Fujiwara, Masahiro et al, "Mechanistic Studies of Tetraphenylstibonium Iodide–Catalyzed Cycloaddition of Oxiranes with Heterocumulenes," *Bull. Chem. Soc. Jpn.*, vol. 63, 1990, pp. 1069–1073.

(List continued on next page.)

*Primary Examiner*—Mukund J. Shah
*Assistant Examiner*—Pavanaram K Sripada
*Attorney, Agent, or Firm*—Oliff & Berridge, PLC

[57] ABSTRACT

The present invention produces novel cis-oxazolidinone compound which is racemic form or optically active form, of a formula (1)

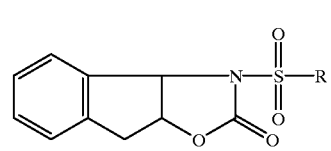

(1)

wherein R represents $C_1$–$C_6$ alkyl group, $C_2$–$C_6$ alkenyl group, $C_1$–$C_6$ alkoxyl group, $C_1$–$C_6$ alkylamino group, aryl group or halogen atom, and oxazolidinone ring is at cis-configuration, comprising reacting cis-1,2-indene epoxide of a formula (3)

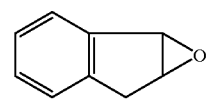

(3)

form, with sulfonyl isocyanate compound of a formula (4)

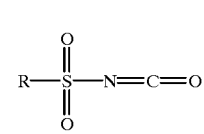

(4)

in the presence of metal halide catalyst.

Further, cis-1-amino-2-indanol is produced by hydrolyzing the oxazolidinone compound. The latter compound is useful as an intermediate of HIV-drug.

23 Claims, No Drawings

OTHER PUBLICATIONS

Ghosh, Arun K. et al, "A Convenient Enzymatic Route to Optically Active 1–Aminoindan–2–ol: Versatile Ligands for HIV–1 Protease Inhibitors and Asymmetric Syntheses," *Synthesis*, vol. 5, May 1997, pp. 541–544.

Davies, Ian W. et al., "Highly Diastereoselective Diels–Alder Reaction Mediated by a Chiral Auxiliary Derived from Amino Indanol: The Role of Conformation on Diastereoselectivity," *Tetrahedron Letters*, vol. 36, No. 42, 1995, pp. 7619–7622.

Didier, Eric et al., "Chemo–Enzymatic Synthesis of 1,2– and 1,3– Amino–Alcohols and Their Use in the Enantioselective Reduction of Acetophenone and Anti–Actophenone Oxime Methyl Ether with Borane," *Tetrahedron*, vol. 47, No. 27, 1991, pp. 4941–4958.

OXAZOLIDINONE COMPOUNDS AND PROCESS FOR THE PREPARATION THEREOF

This is a Continuation-in-Part of Application No. PCT/JP97/02342 filed Jul. 7, 1997. The entire disclosure of the prior application is hereby incorporated by reference herein in its entirety.

FIELD OF THE INVENTION

The present invention relates to a process for producing a cis-1-amino-2-indanol which is useful as an intermediate for drugs and agricultural chemicals, a novel cis-oxazolidinone compound which is an intermediate of the cis-1amino-2-indanol, and a process for producing the compound.

DESCRIPTION OF RELATED ART

Cis-1-amino-2-indanol is important as an intermediate of drugs.

For example, J. Med. Chem., 35, 2525 (1992), J. Med. Chem. 35, 1702 (1992) and J. Med. Chem., 35, 1685,(1992) discloses that this compound is an intermediate of anti-HIV drugs.

There are several conventional processes for producing cis-1-amino-2-indanol.

For example, in J. Am. Chem. Soc., 73, 1639 (1951), trans-phenyloxazoline compound is formed from bromoindanol via trans-1-amino-2-indanol, and the compound is inverted to cis-form, thereby obtaining cis-1amino-2-indanol.

In J. Org. Chem., 32, 540 (1967), iodoisocyanate is added to indene to prepare trans-oxazolidinone compound via trans-iodocarbamate, and the compound is inverted to cis-form, whereby obtaining cis-1-amino-2-indanol.

Japanese Patent Application Laid-open No. Hei 7-316106 discloses a synthesis of cis-oxazoline compound from 1,2-di-substituted indans or cis-1,2-indene epoxide by utilizing Ritter reaction and a process for producing cis-1amino-2-indanol by hydrolysis of the cis-oxazoline compound.

It is known that epoxy compound provides addition products by reacting with heterocumulene compound under the presence of metallic catalyst.

For example, J. Org. Chem., 51, 2177 (1986), Chem. Lett., 1986, 1963 and Bull. Chem. Soc. Jpn., 63, 1069 (1990) disclose syntheses of oxazolidinone compounds by addition reaction of various kinds of epoxy compounds with isocyanate which is heterocumulene compound.

The above-mentioned process via trans-oxazolidinone derivative has such defects that many preparation steps are required due to the necessity of inversion to cis-form, high temperature is needed, volume efficiency and yield are low, and a great quantity of wastes generate.

SUMMARY OF THE INVENTION

As a result that the present inventors made extensive investigation on processes of producing cis-1-amino-2-indanol more efficiently, they found new cis-oxazolidinone compound, a process of producing it and a process for producing amino-alcohol by hydrolysis reaction of said compound, and completed the present invention.

Namely, the present invention relates to cis-oxazolidinone compound which is racemic form or optically active form, of a formula (1)

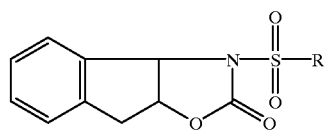

(1)

wherein R represents substituted or unsubstituted $C_1$-$C_6$ alkyl group (the substituent represents $C_1$-$C_6$ alkyl group, $C_1$-$C_6$ alkoxy group, $C_2$-$C_7$ alkoxycarbonyl group, $C_2$-$C_7$ alkylcarbonyloxy group, $C_2$-$C_7$ alkanoyl group, phenyl group or halogen atom), substituted or unsubstituted $C_2$-$C_6$ alkenyl group (the substituent represents $C_1$-$C_6$ alkyl group, $C_1$-$C_6$ alkoxy group, $C_2$-$C_7$ alkoxycarbonyl group, $C_2$-$C_7$ alkylcarbonyloxy group, $C_2$-$C_7$ alkanoyl group, phenyl group or halogen atom), substituted or unsubstituted $C_1$-$C_6$ alkoxyl group (the substituent represents $C_1$-$C_6$ alkyl group, $C_1$-$C_6$ alkoxy group, $C_2$-$C_7$ alkoxycarbonyl group, $C_2$-$C_7$ alkylcarbonyloxy group, $C_2$-$C_7$ alkanoyl group, phenyl group or halogen atom), substituted or unsubstituted $C_1$-$C_6$ alkylamino group (the substituent represents $C_1$-$C_6$ alkyl group, $C_1$-$C_6$ alkoxy group, $C_2$-$C_7$ alkoxycarbonyl group, $C_2$-$C_7$ alkylcarbonyloxy group, $C_2$-$C_7$ alkanoyl group, phenyl group or halogen atom), substituted or unsubstituted aryl group (the substituent represents $C_1$-$C_6$ alkyl group, $C_1$-$C_6$ alkoxy group, $C_2$-$C_7$ alkoxycarbonyl group, $C_2$-$C_7$ alkylcarbonyloxy group, $C_2$-$C_7$ alkanoyl group, phenyl group or halogen atom) or halogen atom, and oxazolidinone ring is at cis-configuration, especially, cis-oxazolidinone compound being an optically active oxazolidionone compound of a formula (2)

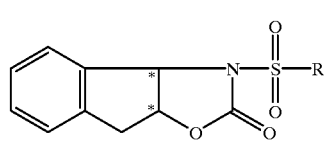

(2)

wherein * means asymmetric carbon atom and the absolute configuration of the carbon atom means R or S, and substituent R has the same meaning as defined in the formula (1).

Moreover, the present invention relates to a process for producing cis-oxazolidinone compound of the formula (1) comprising reacting cis-1,2-indene epoxide which is racemic form or optically active form, of a formula (3)

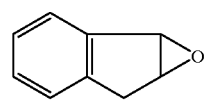

(3)

wherein epoxy ring is at cis-configuration, with sulfonyl isocyanate compound of a formula (4)

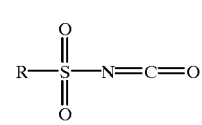

(4)

wherein R has the same meaning as defined in the formula (1), in the presence of metal halide catalyst.

Furthermore, the present invention relates to a process for producing cis-1amino-2-indanol which is racemic form or optically active form of the formula (5)

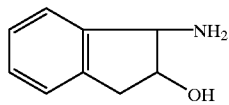
(5)

wherein NH₂ group and OH group are at cis-configuration, by hydrolysis of the cis-oxazolidinone compound of the formula (1).

DETAILED DESCRIPTION OF PREFERRED EMBODIMENTS

The present invention is explained in detail below.

The substituent R is first explained.

The $C_1$–$C_6$ alkyl group includes methyl group, ethyl group, n-propyl group, i-propyl group, n-butyl group, i-butyl group, sec-butyl group, tert-butyl group, n-amyl group, i-amyl group, neopentyl group, n-hexyl group and cyclohexyl group.

The $C_1$–$C_6$ alkoxy group includes methoxy group, ethoxy group, n-propoxy group, i-propoxy group, n-butoxy group, i-butoxy group, sec-butoxy group, tert-butoxy group, n-amyloxy group, i-amyloxy group, neopentyloxy group, n-hexyloxy group and cyclohexyloxy group.

The $C_2$–$C_7$ alkoxycarbonyl group includes methoxycarbonyl group, ethoxycarbonyl group, n-propoxycarbonyl group, i-propoxycarbonyl group, n-butoxycarbonyl group, i-butoxycarbonyl group, sec-butoxycarbonyl group, n-amyloxycarbonyl group, i-amyloxycarbonyl group, neopentyloxycarbonyl group, n-hexyloxycarbonyl group and cyclohexyloxycarbonyl group.

The $C_2$–$C_7$ alkylcarbonyloxy groups includes methylcarbonyloxy group, ethylcarbonyloxy group, n-propylcarbonyloxy group, i-propylcarbonyloxy group, n-butylcarbonyloxy group, i-butylcarbonyloxy group, sec-butylcarbonyloxy group, tert-butylcarbonyloxy group, n-amylcarbonyloxy group, i-amylcarbonyloxy group, neopentylcarbonyloxy group, n-hexylcarbonyloxy group and cyclohexylcarbonyloxy group.

The $C_2$–$C_7$ alkanoyl groups includes acetyl group, ethylcarbonyl group, n-propylcarbonyl group, i-propylcarbonyl group, n-butylcarbonyl group, i-butylcarbonyl group, sec-butylcarbonyl group, n-amylcarbonyl group, i-amylcarbonyl group, neopentylcarbonyl group, n-hexylcarbonyl group and cyclohexylcarbonyl group.

The $C_2$–$C_6$ alkenyl groups includes vinyl group, isopropenyl group, allyl group, methallyl group, 1-butenyl group, 3-hexenyl group, 1-cyclopentenyl group, 1-cyclohexenyl group, methoxyvinyl group and ethoxyvinyl group.

The $C_1$–$C_6$ alkylamino group includes monoalkylamino group and dialkylamino group.

Concrete examples of the $C_1$–$C_6$ alkylamino group are methylamino group, ethylamino group, n-propylamino group, i-propylamino group, n-butylamino group, i-butylamino group, sec-butylamino group, tert-butylamino group, n-amylamino group, i-amylamino group, neopentylamino group, n-hexylamino group, cyclohexylamino group, dimethylamino group and diethylamino group.

The aryl group includes phenyl group, o-tolyl group, m-tolyl group, p-tolyl group, 3,5-dimethylphenyl group, 2,4,6-trimethylphenyl group, 2,4,6-tri-i-propylphenyl group, 4-i-propylphenyl group, 4-tert-butylphenyl group, 4-methoxyphenyl group, 3,5-dimethoxyphenyl group, 2-fluorophenyl group, 3-fluorophenyl group, 4-fluorophenyl group, 2-chlorophenyl group, 3-chlorophenyl group, 4-chlorophenyl group, 2-bromophenyl group, 3-bromophenyl group, 4-bromophenyl group, 2,4-dichlorophenyl group, 4-phenylphenyl group, 1-naphthyl group, 2-naphthyl group, 1-anthracenyl group, 2-anthracenyl group, 5-anthracenyl group, 2-pyridyl group, 3-pyridyl group and 4-pyridyl group.

The halogen atom includes fluorine atom, chlorine atom, bromine atom and iodine atom.

The following is an explanation of the addition reaction of the cis-1,2-indene epoxide of the formula (3) with sulfonyl isocyanate compound of the formula (4).

The cis-1,2-indene epoxide of the formula (3) includes racemic form and optically active form of (+)-cis-1,2-indene epoxide and (−)-cis-1,2-indene epoxide.

The sulfonyl isocyanate compound of the formula (4) includes methanesulfonyl isocyanate, ethanesulfonyl isocyanate, n-propanesulfonyl isocyanate, n-butanesulfonyl isocyanate, trifluoromethanesulfonyl isocyanate, benzenesulfonyl isocyanate, p-toluenesulfonyl isocyanate and chlorosuflonyl isocyanate. Preferred are methanesulfonyl isocyanate and p-toluenesulfonyl isocyanate.

The amount of the sulfonyl isocyanate compound used of the formula (4) is in the range of 0.1 to 10 times molar quantity, preferably, 0.5 to 5 times molar quantity, to the cis-1,2-indene epoxide of the formula (3).

The metal halide catalyst includes alkali metal halide compound, tin halide compound and zinc halide compound.

The alkali metal halide compound includes lithium halide, sodium halide and potassium halide.

Concretely, it is raised lithium bromide, lithium iodide, sodium chloride, sodium bromide, sodium iodide, potassium chloride, potassium bromide and potassium iodide.

The tin halide compound includes tin halide, alkyltin halide and phenyltin halide.

Concretely, it is raised tin chloride, tin bromide, tin iodide, dimethyltin chloride, dimethyltin bromide, dimethyltin iodide, diethyltin chloride, diethyltin bromide, diethyltin iodide, di-n-propyltin chloride, di-n-propyltin bromide, di-n-propyltin iodide, di-n-butyltin chloride, di-n-butyltin bromide, di-n-butyltin iodide, diphenyltin chloride, diphenyltin bromide, diphenyltin iodide, trimethyltin chloride, trimethyltin bromide, trimethyltin iodide, triethyltin chloride, triethyltin bromide, triethyltin iodide, tri-n-propyltin chloride, tri-n-propyltin bromide, tri-n-propyltin iodide, tri-n-butyltin chloride, tri-n-butyltin bromide, tri-n-butyltin iodide, tri-n-phenyltin chloride, tri-n-phenyltin bromide, tri-n-phenyltin iodide. Preferred are tin iodide, dimethyltin iodide and di-n-butyltin iodide.

The zinc halide compound includes zinc chloride, zinc bromide and zinc iodide.

In the present invention, the reaction can be conducted in the co-existence with Lewis base so as to facilitate the reaction.

The Lewis base includes amines such as triethylamine, tri-n-butylamine, 1,8-diazabicyclo [5,4,0]-7-undecene (DBU) and 1,5-diazabicyclo [4,3,0]-5-nonene (DBN), pyridines such as pyridine, picoline, lutidine and methyl ethyl pyridine, pyridine-N-oxides such as pyridine-N-oxide, picoline-N-oxide, lutidine-N-oxide and 4-phenylpyridine-N-oxide, phosphines such as triphenyl phosphine and tri-n- butylphosphine, phosphine oxides such as triphenylphosphineoxide and tri-n-butylphosphine oxide, phosphonium salts such as tetra-n-butylphosphonium bromide, tetraphenylphosphonium bromide, tetra n-butyl-phosphonium iodide and tetraphenylphosphonium iodide, sulfoxides such as dimethyl sulfoxide, diethyl sulfoxide, di-n-propyl sulfoxide and diphenyl sulfoxide, ureas such as tetramethyl urea, tetrabutyl urea and dimethylpropyl urea, hexamethylphosphoric triamide (HMPA), 2,2'-azobisisobutylnitrile (AIBN). Preferred are tri-n-butylphosphine oxide, tetrabutyl urea and hexamethylphosphoric triamide (HMPA).

The amount of the metal halide compound used is in the range of from 0.1 to 50 mol %, preferably, from 1 to 20 mol %, to the cis-1,2-indene epoxide of the formula (3).

The amount of Lewis base used is in the range of from equimolar amount to 5 mole times, preferably, from equimolar to 3 mole times, to the metal halide compound.

The reaction solvent is not particularly limited so long as it does not participate in the reaction.

Examples of the reaction solvent are nitriles such as acetonitrile, propionitrile and butyronitrile, ketones such as acetone, methyl ethyl ketone and methyl isobutyl ketone, aromatic hydrocarbons such as benzene, toluene, xylene, mesitylene, chlorobenzene and o-dichlorobenzene, aliphatic hydrocarbons such as n-hexane, cyclohexane, n-octane and n-decane, esters such as methyl acetate, ethyl acetate and butyl acetate, halogenated hydrocarbons such as dichloromethane, dichloroethane, chloroform and carbon tetrachloride, ethers such as tetrahydrofuran, diethyl ether, t-butyl methyl ether and dimethoxyethane, alcohols such as methanol, ethanol, 1-propanol, 2-propanol, 1-butanol, 2-butanol, isobutanol and cyclohexanol, amides such as N,N-dimethylformamide, N,N-dimethylacetamide and N-methyl pyrrolidone, and ureas such as 1,3-dimethyl imidazolidinone, tetramethyl urea and tetrabutyl urea. Preferred are toluene, cyclohexane, ethyl acetate and tetrabutyl urea.

These solvents can be used singly or in combination.

The reaction temperature is not particularly limited, and can employ from −20° C. to a boiling point of a solvent to be used. However, the reaction is preferably conducted in the range of from 20° C. to 100° C.

The reaction time is normally from 0.1 to 1000 hours, although varying depending on the reactivity of the sulfonyl isocyanate compound of the formula (4).

After completion of the reaction, water is added and extraction is conducted by a suitable solvent, and the solvent is concentrated under reduced pressure to obtain a crude product, or a solid is precipitated from a suitable solvent to obtain a crude product.

Further, a pure cis-oxazolidinone compound of the formula (1) can be obtained by conducting purification by usual process such as recrystallization or silica gel column chromatography and so on.

Hydrolysis reaction of the cis-oxazolidinone compound of the formula (1) is then explained.

In the hydrolysis reaction, an acid or an alkali is used.

The acid includes inorganic acids such as hydrochloric acid, sulfuric acid, phosphoric acid, nitric acid, hydrobromic acid, hydroiodic acid and hydrofluoric acid, carboxylic acids such as formic acid, acetic acid, trichloroacetic acid and trifluoroacetic acid, sulfonic acids such as p-toluenesulfonic acid, methanesulfonic acid and trifluoromethanesulfonic acid.

The alkali includes hydroxides of alkali metals or alkaline earth metals such as sodium hydroxide, potassium hydroxide, lithium hydroxide, magnesium hydroxide, calcium hydroxide and barium hydroxide, carbonates of alkali metals or alkaline earth metals such as sodium carbonate, potassium carbonate, lithium carbonate, magnesium carbonate, calcium carbonate and barium carbonate. These alkalis can be used in aqueous solution.

The amount of acid or alkali used is normally equimolar amount or more to the cis-oxazolidinone compound of the formula (1). In order to complete the hydrolysis reaction in a short time, large excess amount up to about 20 times molar quantity may be used.

The reaction can be conducted in an acid or alkali aqueous solution, but can be conducted in an organic solvent.

The organic solvent is not particularly limited so long as it does not participate in the reaction. The organic solvent includes ketones such as acetone, methyl ethyl ketone, methyl isobutyl ketone, aromatic hydrocarbons such as benzene, toluene, xylene, mesitylene, chlorobenzene and o-dichlorobenzene, aliphatic hydrocarbons such as n-hexane, cyclohexane, n-octane and n-decane, halogenated hydrocarbons such as dichloromethane, dichloroethane, chloroform and carbon tetrachloride, ethers such as tetrahydrofuran, diethyl ether, t-butyl methyl ether, dimethoxyethane and dioxane, alcohols such as methanol, ethanol, 1-propanol, 2-propanol, 1-butanol, 2-butanol, isobutanol and cyclohexanol. Preferred are acetone, ethanol and dioxane.

These solvents can be used singly or in combination.

The hydrolysis temperature is not particularly limited, but it is normally possible from 0° C. to a boiling point of a solvent to be used, preferably, from 20° C. to 100° C.

The reaction times are normally from 0.1 to 1000 hours.

After completion of the hydrolysis, extraction is conducted in the usual method by adding water and a suitable solvent, and the solvent is concentrated under reduced pressure to obtain a crude product, or a solid is precipitated from a suitable solvent to obtain a crude product.

Further, a pure cis-1amino-2-indanol compound of the formula (5) can be obtained by conducting purification in usual process such as recrystallization or silica gel column chromatography and so on.

BEST METHOD TO CARRY OUT THE INVENTION

The present invention will be hereinbelow explained in more detail by referring to examples. However, the present invention is not limited by these examples.

EXAMPLE 1

Synthesis of cis-N-p-toluenesulfonylindano[1,2-d]oxazolidin-2-one (6)

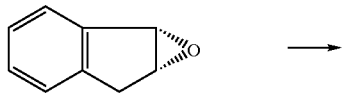

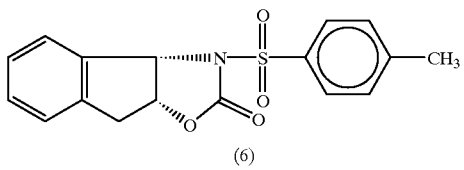

(6)

To 50 ml of toluene were added 5.00 g of (+)-cis-1,2-indene epoxide (34 mmole, 89.4% in purity, 90.2% ee in optical purity), 1.65 g (10 mol % to the above-mentioned epoxide) of di-n-butyltin iodide (n-Bu$_2$SnI$_2$) and 0.606 g (10 mol % to the above-mentioned epoxide) of hexamethylphosphoric triamide (HMPA) under an argon atmosphere. The resulting mixture was heated to 50 to 60° C., and 25 ml of toluene solution of 6.67 g (34 mmole) of p-toluenesulphonyl isocyanate were dropwise added to the mixture over one hour.

After the mixture was stirred at 60° C. for three hours, the mixture was further stirred under reflux for one hour.

After the reaction liquid was concentrated under reduced pressure and acetonitrile was added thereto to be completely dissolved therein, the intended product in the solution was determined with a liquid chromatography (column: Inertsil ODS-2 4.6φ×250 mm, column temperature: 40° C., eluent: acetonitrile/water=50/50, flow rate: 1.0 ml/min., detection: UV254 nm). The content of the intended product was 9.99 g (yield: 90%).

The solution was concentrated and then recrystallized from acetonitrile to obtain 6.0 g of purified product.

The optical purity of the purified product was 98.4% ee. (HPLC, column: Chiralcel OJ-R 4.6φ×250 mm, column temperature: 35° C., eluent: acetonitrile/water=50/50, flow rate: 0.5 ml/min., detection: UV254 nm).

Melting point: 183.0–185.0° C.

$^1$H NMR(CDCl$_3$ 400 MHz): 7.96–7.93(3H,m), 7.40–7.26 (5H,m), 5.88(1H,d,J=7.3 Hz), 5.31(1H,ddd,J=7.3, 5.8, 1.3 Hz), 3.39(1H, dd, J=5.8, 17.9 Hz), 3.31(1H,dd,J=1.3, 17.9 Hz), 2.42(3H,s).

IR(KBr): 2991, 1781, 1595, 1351, 1171, 1140, 1023, 815, 758, 666 cm$^{-1}$.

MS m/z(rel. Int.) 329(M+, 5), 174(25), 146(100).

EXAMPLE 2

Synthesis of Cis-N-methanesulfonyl indano[1,2-d] oxazolidin-2-one (7)

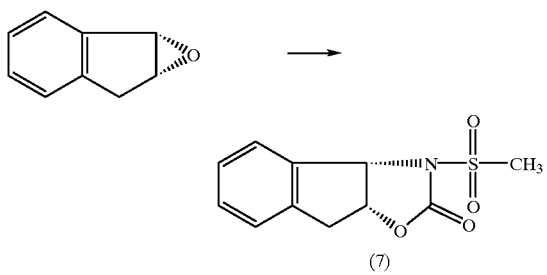

(7)

Reaction and post-treatment were conducted in the same manner as in the Example 1 except that 4.12 g (34 mmole) of methanesulfonyl isocyanate was used in place of p-toluenesulfonyl isocyanate to obtain 6.00 g of the intended product (yield: 70%).

Melting point: 168.2–168.9° C.

$^1$H NMR(CDCl$_3$ 400 MHz): 7.78(1H,d,J=8.0Hz), 7.45–7.25(3H,m), 5.88(1H,d,J=7.2 Hz), 5.45–5.40(1H,m), 3.41(2H,d,J=3.2 Hz), 3.32(3H,s).

IR(KBr):1777, 1358, 1162, 1037, 983, 762, 564, 520 cm$^{-1}$.

MS m/z(rel. Int.) 253(M+, 15), 174(30), 146(15), 130 (100), 104(70).

EXAMPLES 3 TO 8

Reaction and post-treatment were conducted in the same manner as in the Example 1 except that reaction solvents were varied to obtain cis-N-p-toluenesulfonylindano[1,2-d] oxazolidin-2-one (6). The results are shown in the following table.

TABLE 1

| Example | Solvent | Yield (%) |
|---|---|---|
| 3 | tetrahydrofuran | 70 |
| 4 | benzene | 88 |
| 5 | cyclohexane | 54 |
| 6 | ethyl acetate | 48 |
| 7 | chloroform | 23 |
| 8 | acetonitrile | 18 |

EXAMPLES 9 TO 19

Reaction and post-treatment were conducted in the same manner as in the Example 1 except that various kinds of metal halide compounds (10 mol % of the above-mentioned epoxide) were used in place of di-n-butyltin iodide and various kinds of Lewis bases (20 mol % of the above-mentioned epoxide, but only tetramethyl urea 10 mol %) were used in place of hexamethylphosphoric triamide (HMPA) to obtain cis-N-p-toluenesulfonylindano[1,2-d] oxazolidin-2-one (6). The shown in the following table.

TABLE 2

| Example | Metal halide | Lewis base | Yield (g) | Yield (%) |
|---|---|---|---|---|
| 9 | SnI$_2$ | triphenylphosphine | 4.5 | 40 |
| 10 | n-Bu$_2$SnI$_2$ | triethylamine | 2.9 | 26 |
| 11 | LiBr | HMPA | 8.7 | 78 |
| 12 | LiBr | tri-n-butyl-phosphine oxide | 8.4 | 75 |
| 13 | LiI | HMPA | 7.9 | 71 |
| 14 | ZnI$_2$ | HMPA | 7.1 | 63 |
| 15 | NaI | HMPA | 10.1 | 90 |
| 16 | KI | HMPA | 7.1 | 64 |
| 17 | NaI | tetramethyl urea | 2.2 | 20 |
| 18 | NaI | 4-phenylpyridine-N-oxide | 5.3 | 47 |
| 19 | NaI | tri-n-butyl-phosphine oxide | 9.2 | 82 |

EXAMPLE 20

To 30 ml of tetrabutyl urea suspension containing 324 mg (10 mol % to the below-mentioned epoxide) of sodium iodide were added 3.00 g of (+)-cis-1,2-indene epoxide (22 mmol, 96% in purity, 90% ee in optical purity) under an argon atmosphere at 25° C. After the mixture was stirred at 25° C. for thirty minutes, it was heated to 45° C.

To the mixed liquid were dropwise added 15 ml of tetrabutyl urea solution containing 4.56 g (23 mmole) of p-toluenesulfonyl isocyanate at 45 to 50° C. over one hour.

Thereafter, the resulting mixture was further stirred at this temperature for three hours.

The reaction mixed liquid was added with hexamethylphosphoric triamide and acetonitrile and completely dissolved therein. Thereafter, the intended product in the solution was determined with a liquid chromatography (column: Inertsil ODS-2 4.6φ×250 mm, column temperature: 40° C., eluent: acetonitrile/water=60/40 (0.2% acetic acid), flow rate: 1.0 ml/min., detection: UV254 nm). As a result, the content of the intended product was 7.10 g (yield: 99%).

EXAMPLE 21

To 125 ml of tetrabutyl urea suspension containing 2.89 g (10 mol % to the below-mentioned epoxide) of sodium iodide were added 25.0 g of (+)-cis-1,2-indene epoxide (0.153 mole, 81% in purity, 93% ee in optical purity) at 25° C. under an argon atmosphere. After the mixture was stirred at 25° C. for thirty minutes, it was heated to 45° C.

To the mixed liquid were added 31.7 g (0.161 mole) of p-toluenesulfonyl isocyanate at 45 to 50° C. over one hour. Thereafter, the mixture was further stirred at this temperature for three hours.

After the reaction mixed liquid was cooled to 4° C., precipitates were filtered off, and crystals were washed with methanol.

The crystals obtained were dried to obtain 46.2 g of the intended product (purity: 98%, yield: 90%).

The optical purity of the crystals obtained was 98% ee. (HPLC, column: Chiralcel OJ-R 4.60φ×250 mm, column temperature: 35° C., eluent: acetonitrile/methanol/water=3/2/5, flow rate: 0.9 ml/min., detection: UV254 nm).

EXAMPLE 22

Synthesis of (−)cis-1amino-2-indanol (8)

1 ml of 97% sulfuric acid was added to 1.00 g (3.0 mmole, 99% in purity, 100% ee in optical purity) of cis-N-p-toluenesulfonylindano[1,2-d]oxazolidine-2-one (6) and stirred at 60° C. for one hour.

Then, an aqueous sodium hydroxide solution was added to the mixture and pH was adjusted to 10 to 11. After the mixture was stirred at 80° C. for thirty minutes, extraction was conducted by adding chloroform.

The chloroform layer was dried by sodium sulfate and then concentrated to obtain 0.41 g of the intended product (yield: 91%). Optical purity was 100% ee.

EXAMPLE 23

Reaction and post-treatment were conducted in the same manner as in the Example 17 except that 3 ml of an aqueous solution of 40% sodium hydroxide were used in place of sulfonic acid and stirring was conducted under reflux for three days to obtain 0.16 g of (−)-cis-1-amino-2-indanol (8) (yield: 35%). Optical purity was 100% ee.

EXAMPLE 24

28 g of 85% sulfonic acid were added to 9.9 g (29 mmole, 96.7% in purity, 100% ee in optical purity) of cis-N-p-toluenesulfonylindano[1,2-d]oxazolidin-2-one (6) under an argon atmosphere and stirred at 72° C. for three hours.

After the mixture was cooled to 20° C., 51 g of water was added to the mixture and precipitated crystals were filtered.

The crystals obtained were washed with water and then, the crystals were dried under reduced pressure to obtain 5.16 g (92% in purity, yield: 94%) of oxazolidinone intermediate (cis[1,2-d]oxazolidin-2-one).

3.26 g (17.1 mmole) of the oxazolidinone intermediate were added to an aqueous solution of 1.44 g of sodium hydroxide dissoved in 15.0 g of water under an argon atmosphere, and the mixture was stirred at 85° C. for six hours.

After completion of the reaction, the mixture was added with chloroform and extracted, and the chloroform layer was concentrated to obtain 2.54 g of the intended product (yield: 99%).

Optical purity was 100% ee.

INDUSTRIAL APPLICABILITY

According to the present invention, novel cis-oxazolidinone compound of the formula (1) can be readily produced from cis-1,2-indene epoxide of the formula (3) and sulfonyl isocyanate compound of the formula (4) and further, cis-1amino-2-indanol of the formula (5) can be produced by hydrolyzing the cis-oxazolidinone compound. The cis-1amino-2-indanol of the formula (5) is useful for an intermediate of drugs, e.g., HIV-drug.

What is claimed is:

1. A cis-oxazolidinone compound that is in a racemic form or optically active form, of a formula (1)

(1)

wherein R is selected from the group consisting of substituted or unsubstituted $C_1$–$C_6$ alkyl group (the substituent is selected from the group consisting of $C_1$–$C_6$ alkyl group, $C_1$–$C_6$ alkoxy group, $C_2$–$C_7$ alkoxycarbonyl group, $C_2$–$C_7$ alkylcarbonyloxy group, $C_2$–$C_7$ alkanoyl group, phenyl group and halogen atom), substituted or unsubstituted $C_2$–$C_6$ alkenyl group (the substituent is selected from the group consisting of $C_1$–$C_6$ alkyl group, $C_2$–$C_6$ alkoxy group, $C_2$–$C_7$ alkoxycarbonyl group, $C_2$–$C_7$ alkylcarbonyloxy group, $C_2$–$C_7$ alkanoyl group, phenyl group, and halogen atom), substituted or unsubstituted $C_1$–$C_6$ alkoxyl group (the substituent is selected from the group consisting of $C_1$–$C_6$ alkyl group, $C_1$–$C_6$ alkoxy group, $C_2$–$C_7$ alkoxycarbonyl group, $C_2$–$C_7$ alkylcarbonyloxy group, $C_2$–$C_7$ alkanoyl group, phenyl group and halogen atom), substituted or unsubstituted $C_1$–$C_6$ alkylamino group (the substituent is selected from the group consisting of $C_1$–$C_6$ alkyl group, $C_1$–$C_6$ alkoxy group, $C_2$–$C_7$ alkoxycarbonyl group, $C_2$–$C_7$ alkylcarbonyloxy group, $C_2$–$C_7$ alkanoyl group, phenyl group and halogen atom), substituted or unsubstituted aryl group (the substituent is selected from the group consisting of $C_1$–$C_6$ alkyl group, $C_1$–$C_6$ alkoxy group, $C_2$–$C_7$ alkoxycarbonyl group, $C_2$–$C_7$ alkylcarbonyloxy group, $C_2$–$C_7$ alkanoyl group, phenyl group, and halogen atom), and halogen atom, and wherein the oxazolidinone ring is at cis-configuration.

2. The compound as claimed in claim 1, wherein the cis-oxazolidinone compound is an optically active oxazolidionone compound of a formula (2)

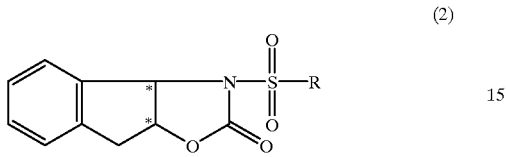

(2)

wherein * means asymmetric carbon atom and the absolute configuration of the carbon atom means R or S, and substituent R has the same meaning as defined in the formula (1).

3. The compound as claimed in claim 2, wherein R in the optically active oxazolidionone represents p-tolyl group.

4. A process for producing cis-oxazolidinone compound of the formula (1)

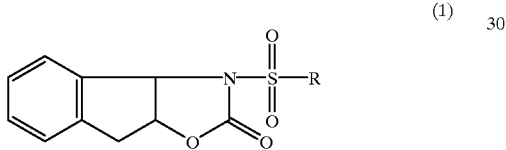

(1)

wherein R is selected from the group consisting of substituted or unsubstituted $C_1$–$C_6$ alkyl group (the substituent is selected from the group consisting of $C_1$–$C_6$ alkyl group, $C_1$–$C_6$ alkoxy group, $C_2$–$C_7$ alkoxycarbonyl group, $C_2$–$C_7$ alkylcarbonyloxy group, $C_2$–$C_7$ alkanoyl group, phenyl group and halogen atom), substituted or unsubstituted $C_2$–$C_6$ alkenyl group (the substituent is selected from the group consisting of $C_1$–$C_6$ alkyl group, $C_1$–$C_6$ alkoxy group, $C_2$–$C_7$ alkoxycarbonyl group, $C_2$–$C_7$ alkylcarbonyloxy group, $C_2$–$C_7$ alkanoyl group, phenyl group and halogen atom), substituted or unsubstituted $C_1$–$C_6$ alkoxyl group (the substituent is selected from the group consisting of $C_1$–$C_6$ alkyl group, $C_1$–$C_6$ alkoxy group, $C_2$–$C_7$ alkoxycarbonyl group, $C_2$–$C_7$ alkylcarbonyloxy group, $C_2$–$C_7$ alkanoyl group, phenyl group and halogen atom), substituted or unsubstituted $C_1$–$C_6$ alkylamino group (the substituent is selected from the group consisting of $C_1$–$C_6$ alkyl group, $C_1$–$C_6$ alkoxy group, $C_2$–$C_7$ alkoxycarbonyl group, $C_2$–$C_7$ alkylcarbonyloxy group, $C_2$–$C_7$ alkanoyl group, phenyl group, and halogen atom), substituted or unsubstituted aryl group (the substituent is selected from the group consisting of $C_1$–$C_6$ alkyl group, $C_1$–$C_6$, alkoxy group, $C_2$–$C_7$ alkoxycarbonyl group, $C_2$–$C_7$alkylcarbonyloxy group, $C_2$–$C_7$alkanoyl group, phenyl group, and halogen atom) and halogen atom, and wherein the oxazolidinone ring is at cis-configuration, said process comprising reacting cis-1,2-indene epoxide, which is in a racemic form or optically active form, of a formula (3)

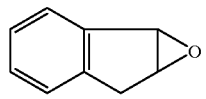

(3)

wherein epoxy ring is at cis-configuration, with sulfonyl isocyanate compound of a formula (4)

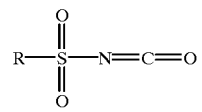

(4)

wherein R has the same meaning as defined in the formula (1), in the presence of metal halide catalyst selected from the group consisting of alkali metal halide compound, tin halide compound and zinc halide compound.

5. A process for producing cis-1amino-2-indanol, which is in a racemic form or optically active form, of the formula (5)

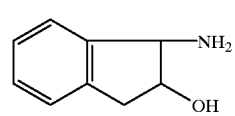

(5)

wherein $NH_2$ group and OH group are at cis-configuration, said process comprising:

obtaining a cis-oxazolidinone compound of the formula (1)

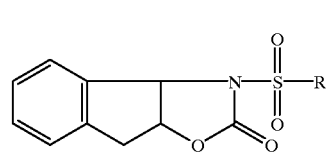

(1)

wherein R is selected from the group consisting of substituted or unsubstituted $C_1$–$C_6$ alkyl group (the substituent is selected from the group consisting of $C_1$–$C_6$ alkyl group, $C_1$–$C_6$ alkoxy group, $C_2$–$C_7$ alkoxycarbonyl group, $C_2$–$C_7$ alkylcarbonyloxy group, $C_2$–$C_7$ alkanoyl group, phenyl group and halogen atom), substituted or unsubstituted $C_2$–$C_6$ alkenyl group (the substituent is selected from the group consisting of $C_1$–$C_6$ alkyl group, $C_1$–$C_6$ alkoxy group, $C_2$–$C_7$ alkoxycarbonyl group, $C_2$–$C_7$ alkylcarbonyloxy group, $C_2$–$C_7$ alkanoyl group, phenyl group, and halogen atom), substituted or unsubstituted $C_1$–$C_6$ alkoxy group (the substituent is selected from the group consisting of $C_1$–$C_6$ alkyl group, $C_1$–$C_6$ alkoxy group, $C_2$–$C_7$ alkoxycarbonyl group, $C_2$–$C_7$ alkylcarbonyloxy group, $C_2$–$C_7$ alkanoyl group, phenyl group and halogen atom), substituted or unsubstituted $C_1$–$C_6$ alkylamino group (the substituent is selected from the group consisting of $C_1$–$C_6$ alkyl group, $C_1$–$C_6$ alkoxy group, $C_2$–$C_7$ alkoxycarbonyl group, $C_2$–$C_7$ alkylcarbonyloxy group, $C_2$–$C_7$ alkanoyl group, phenyl group and halogen atom), substituted or unsubstituted aryl group (the substituent is selected from the group consisting of $C_1$–$C_6$ alkyl group, $C_1$–$C_6$ alkoxy group, $C_2$–$C_7$ alkoxycarbonyl group, $C_2$–$C_7$ alkylcarbonyloxy group, $C_2$–$C_7$ alkanoyl group, phenyl group and halogen atom) and halogen atom, and wherein the oxazolidinone ring is at cis-configuration, by reacting cis-1,2-indene epoxide, which is in racemic form or optically active form, of a formula (3)

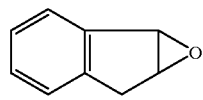

(3)

wherein the epoxy ring is at a cis-configuration, with a sulfonyl isocyanate compound of a formula (4)

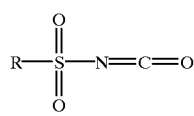

(4)

wherein R has the same meaning as defined in the formula (1), in the presence of metal halide catalyst selected from the group consisting of alkali metal halide compound, tin halide compound and zinc halide compound, and hydrolyzing said oxazolidinone compound.

6. The process for producing cis-oxazolidinone compound as claimed in claim 4, wherein cis-1,2-indene epoxide is an optically active (+)-cis-1,2-indene epoxide.

7. The process for producing cis-oxazolidinone compound as claimed in claim 4, wherein cis-1,2-indene epoxide is an optically active (−)-cis-1,2-indene epoxide.

8. The process for producing cis-oxazolidinone compound as claimed in claim 4, wherein R represents p-tollyl group.

9. The process for producing cis-oxazolidinone compound as claimed in claim 4, wherein the compound of the formula (1) is the compound of the formula

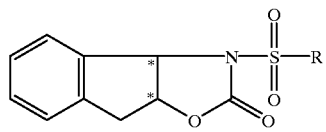

(2)

wherein * means asymmetric carbon atom and the absolute configuration of the carbon atom means R or S, and substituent R has the same meaning as defined in the formula (1).

10. The process for producing cis-oxazolidinone compound as claimed in claim 4, wherein the metal halide catalyst is di-n-butyltin or sodium iodide.

11. The process for producing cis-oxazolidinone compound as claimed in claim 4, wherein said cis-1,2-indene epoxide is reacted with said sulfonyl isocyanate compound in the presence of said metal halide catalyst and at least one Lewis base.

12. The process for producing cis-oxazolidinone compound as claimed in claim 11, wherein the Lewis base is hexamethylphosphoric triamide (HMPA) or tetrabutyl urea.

13. The process for producing cis-oxazolidinone compound as claimed in claim 4, wherein said cis-1,2-indene epoxide of the formula (3) is reacted with p-toluenesulfonylisocyanate in the presence of sodium iodide and tetrabutyl urea to obtain cis-N-p-toluenesulfonylindano oxazolidin-2-one.

14. The process for producing cis-1amino-2-indanol as claimed in claim 5, wherein cis-1,2-indene epoxide is an optically active (+)-cis-1,2-indene epoxide.

15. The process for producing cis-1amino-2-indanol as claimed in claim 5, wherein cis-1,2-indene epoxide is an optically active (−)-cis-1,2-indene epoxide.

16. The process for producing cis-1amino-2-indanol as claimed in claim 5, wherein R represents p-tolyl group.

17. The process for producing cis-1amino-2-indanol as claimed in claim 5, wherein the compound of the formula (1) is the compound of the formula (2)

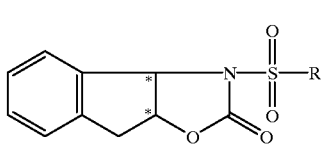

(2)

wherein * means asymmetric carbon atom and the absolute configuration of the carbon atom means R or S, and substituent R has the same meaning as defined in the formula (1).

18. The process for producing cis-1-amino-2-indanol as claimed in claim 5, wherein the metal halide catalyst is di-n-butyltin iodide or sodium iodide.

19. The process for producing cis-1-amino-2-indanol as claimed in claim 5, wherein said cis-1,2-indene epoxide is reacted with said sulfonyl isocyanate compound in the presence of said metal halide catalyst and at least one Lewis base.

20. The process for producing cis-1-amino-2-indanol as claimed in claim 19, wherein the Lewis base is hexamethylphosphoric triamide (HMPA) or tetrabutyl urea.

21. The process for producing cis-1amino-2-indanol as claimed in claim 5, wherein said cis-1,2-indene epoxide of the formula (3) is reacted with p-toluenesulfonylisocyanate in the presence of sodium iodide and tetrabutyl urea to obtain cis-N-p-toluenesulfonylindano oxazolidin-2-one.

22. The process for producing cis-1amino-2-indanol as claimed in claim 5, wherein the oxazolidinone compound of the formula (1) is hydrolyzed in the presence of sulphuric acid.

23. The process for producing cis-1amino-2-indanol as claimed in claim 5, wherein said oxazolidinone compound of the formula (1) is hydrolyzed with acid and subsequently with alkali.

* * * * *